(12) United States Patent
Hunger et al.

(10) Patent No.: US 11,370,037 B2
(45) Date of Patent: Jun. 28, 2022

(54) DEFLECTOR ATTACHMENT FOR A DRILLING TOOL, DRILLING DEVICE, AND CONVERSION SET, AND METHOD FOR CARRYING OUT DRILLING AT LOCATIONS WHICH ARE DIFFICULT TO REACH

(71) Applicant: IML Instrumenta Mechanik Labor GmbH, Wiesloch (DE)

(72) Inventors: Erich Hunger, Karlsruhe (DE); Sebastian Hunger, Leimen (DE); Fabian Hunger, Leimen (DE)

(73) Assignee: IML Instrumenta Mechanik Labor GmbH, Wiesloch (DE)

( * ) Notice: Subject to any disclaimer, the term of this patent is extended or adjusted under 35 U.S.C. 154(b) by 82 days.

(21) Appl. No.: 16/638,542

(22) PCT Filed: Jul. 18, 2018

(86) PCT No.: PCT/EP2018/000360
§ 371 (c)(1),
(2) Date: Feb. 12, 2020

(87) PCT Pub. No.: WO2019/034272
PCT Pub. Date: Feb. 21, 2019

(65) Prior Publication Data
US 2020/0164445 A1    May 28, 2020

(30) Foreign Application Priority Data
Aug. 17, 2017 (DE) .......................... 10 2017 007 725

(51) Int. Cl.
*B23B 45/00* (2006.01)
*G01N 33/46* (2006.01)
*B25F 3/00* (2006.01)

(52) U.S. Cl.
CPC .......... *B23B 45/005* (2013.01); *G01N 33/46* (2013.01); *B25F 3/00* (2013.01); *Y10T 408/05* (2015.01)

(58) Field of Classification Search
CPC ... B23B 4/005; B23B 4/003; B23B 2260/068; G01N 33/46; G01N 3/40;
(Continued)

(56) References Cited

U.S. PATENT DOCUMENTS

RE5,939 E   * 6/1874  Stow .............................. 464/52
369,865 A   * 9/1887  Mann ....................... F16C 1/06
                                                           464/53
(Continued)

FOREIGN PATENT DOCUMENTS

DE          749949 C   * 12/1952   ........... B23B 45/005
DE         297 07 307      2/1998
(Continued)

OTHER PUBLICATIONS

Machine Translation, DE 749949. (Year: 1952).*

*Primary Examiner* — Chwen-Wei Su
(74) *Attorney, Agent, or Firm* — Gudrun E. Huckett

(57) ABSTRACT

The invention relates to a deflector attachment (1), which is designed to be arranged on a predetermined drilling tool (111) having a predetermined drilling needle (19) which can be supported and guided along a drill axis (b) and which protrudes out of a housing (12) of the drilling tool (111) at the front. The deflector attachment (1) can be arranged on the front face of the drilling tool (111) and has a deflecting housing in which, in an arrangement for use, the drilling needle (19) emerging from the housing (12) of the drilling tool (111) can be guided. In the arrangement for use the deflecting housing is curved by a predetermined angle (a) and provides a drilling needle exit axis (a) which is offset by the predetermined angle (a) in relation to the predetermined drill axis (b) of the drilling tool (111). The invention further relates to a drilling device having a deflector attachment according to the invention, to a conversion set for drilling devices, and to a method for carrying out drilling or drill resistance measurements at a predetermined location of an object using the drilling device with deflector attachment.

10 Claims, 10 Drawing Sheets

(58) Field of Classification Search
CPC ... G01N 2203/0053; G01N 2291/0238; G01N 33/0098; Y10T 408/05; B25F 3/00
USPC ........................................ 73/85, 81; 433/112
See application file for complete search history.

(56) References Cited

U.S. PATENT DOCUMENTS

| | | | | |
|---|---|---|---|---|
| 2,305,895 | A * | 12/1942 | Pearson | B23B 45/005 |
| | | | | 408/125 |
| 3,906,636 | A * | 9/1975 | Rainey | A61C 5/40 |
| | | | | 433/102 |
| 4,541,423 | A | 9/1985 | Barber | |
| 5,409,333 | A * | 4/1995 | Hu | B25B 21/007 |
| | | | | 279/14 |
| 5,449,206 | A * | 9/1995 | Lockwood | F16L 11/18 |
| | | | | 138/120 |
| 5,902,107 | A * | 5/1999 | Lowell | A61C 1/12 |
| | | | | 433/130 |
| 9,891,151 | B2 * | 2/2018 | Hunger | G01N 3/58 |
| 2007/0053754 | A1 * | 3/2007 | Hartranft | B23B 45/005 |
| | | | | 408/127 |
| 2011/0168419 | A1 | 7/2011 | Reynolds | |

FOREIGN PATENT DOCUMENTS

| | | |
|---|---|---|
| DE | 100 31 395 | 4/2001 |
| DE | 10 2009 013 069 | 2/2010 |
| DE | 10 2013 001 711 | 8/2014 |
| DE | 10 2016 011 776 | 4/2018 |

* cited by examiner a)

b)

DEFLECTOR ATTACHMENT FOR A DRILLING TOOL, DRILLING DEVICE, AND CONVERSION SET, AND METHOD FOR CARRYING OUT DRILLING AT LOCATIONS WHICH ARE DIFFICULT TO REACH

BACKGROUND OF THE INVENTION

The invention concerns a deflector attachment for a drilling device, which can be in particular a drilling resistance measuring device, and a drilling apparatus that comprises the deflector attachment. Moreover, the invention concerns a conversion set for converting a conventional drilling device or drilling resistance measuring device and a method for carrying out drilling or drilling resistance measurements at locations which are difficult to reach.

From the prior art it is known to examine the condition of bodies with column-shaped or cylindrical cross sections, in particular of trees and wooden poles, for detection of possible defects such as decay or the like by means of drilling resistance measurement. In this context, according to a method of the prior art, the drilling needle of a drilling resistance measuring device can be allowed to penetrate substantially perpendicular to the trunk/pole axis in a defined way and the resistance exerted in this context by the wood can be measured. Strong deviations from an expected resistance or a sudden drop of the mechanical resistance during insertion indicate a defect that may be caused, for example, by erosion or decay. A device for performing such drilling resistance measurements is disclosed in DE 10 031 395 A1.

An attachment device for electric manual drilling machines that serves for performing examinations such as, for example, density measurements on trees is disclosed inter alia in DE 297 07 307 U1. Here, a drilling attachment is connected to a commercially available drilling machine directly or by means of an adapter and coupled by means of a profile shaft so that the energy for driving the drilling attachment can be transmitted onto the drive mechanism thereof.

DE 10 2016 011 776 B3 discloses a device for performing such drilling resistance measurements as well as a needle guiding apparatus therefor. In this context, the needle guiding apparatus is coupled to the drive of the drilling resistance measuring device and is configured to support the needle by means of a scissor arm arrangement during the drilling process and to guide it through aligned passage openings.

For performing drilling resistance measurements at a location that is difficult to reach as in the region of the ground level, DE 10 2013 001 711 A1 discloses carrying out drilling resistance measurements at a predetermined insertion angle that deviates from 90° in relation to the trunk/pole axis. The obtained results are however more difficult to compare and require a more complex evaluation software.

Aside from drilling resistance measurements, there are also cases conceivable where no resistance measurement is to be carried out but only bores are to be introduced into an object at a location that is difficult to reach, for example, for injecting a protective, impregnating, or treatment liquid for prevention or treatment of defects such as decay in wood.

Based on this prior art, it is object of the present invention to provide an apparatus with which a drilling device or a drilling resistance measuring device can be retrofitted or converted for carrying out drilling or drilling resistance measurements even at locations that are difficult to reach.

SUMMARY OF THE INVENTION

This object is solved by a deflector attachment, embodied for arrangement at a predetermined drilling device with a predetermined supportable drilling needle that can be guided along a drill axis and exits from a housing of the drilling device at the front, wherein the deflector attachment is arrangeable at the front side of the drilling device and comprises a deflector housing in which the drilling needle exiting in an arrangement of use from the housing of the drilling device can be guided, wherein the deflector housing, in the arrangement of use, is curved about a predetermined angle and provides a drilling needle exit axis that is offset by the predetermined angle in relation to the predetermined drill axis of the drilling device.

The further object of providing an apparatus for carrying out drilling or drilling resistance measurements even at locations that are difficult to reach is solved by the drilling apparatus comprising a drilling device or a drilling resistance measuring device and a drilling needle that is supported and guided in the drilling device or the drilling resistance measuring device and exits from the housing of the drilling device or drilling resistance measuring device at the front side, characterized in that the drilling apparatus comprises a deflector attachment as claimed, which is arranged at the front side of the housing of the drilling device or drilling resistance measuring device, and whose deflector housing for the drilling needle in the arrangement of use is curved about a predetermined angle, wherein a section of the drilling needle exiting from the deflector attachment can be guided along the drilling needle exit axis that is offset in the arrangement of use by the predetermined angle in relation to the drill axis of the drilling device or drilling resistance measuring device.

A further object of providing an apparatus to enable carrying out drilling or drilling resistance measurements at different locations that are difficult to reach and differ with regard to their position in relation to a working range of the user is solved by a conversion set for converting or retrofitting drilling devices or drilling resistance measuring devices with a supported and guided drilling needle that exits from the housing of the drilling device or of the drilling resistance measuring device at the front side, characterized in that the conversion set comprises at least two deflector attachments as claimed, which differ with regard to the predetermined angle that is determined by the rigid deflector housing of the deflector attachments and/or a length of the deflector attachment and/or the fastening means.

The method for carrying out drilling or drilling resistance measurements at a predetermined location of an object by use of a drilling apparatus as claimed, comprising the steps arranging and fastening a deflector attachment at the front side of the predetermined drilling device or drilling resistance measuring device by means of fastening means present at the deflector attachment and the predetermined drilling device or the drilling resistance measuring device, exchanging the drilling needle of the drilling device or of the drilling resistance measuring device for a drilling needle that is extended by the length of the deflector attachment, placing the drilling apparatus with the deflector attachment against the predetermined location of the object so that the drilling needle exit axis of the deflector attachment is arranged at a predetermined angular position, preferably at a right angle in relation to a longitudinal axis or a surface plane at the location, and carrying out drilling or drilling resistance measurement by allowing a section of the drilling needle exiting from the deflector attachment along the drilling needle exit axis to penetrate at the predetermined location, wherein the drilling needle is deflected by the deflector attachment about the predetermined angle in relation to the drill axis, solves the object of enabling carrying out drilling or drilling resistance measurements at locations that are difficult to reach.

Further embodiments and preferred embodiments of the deflector attachment, of the drilling apparatus, and of the method are disclosed in the respective dependent claims.

In a first embodiment, the deflector attachment according to the invention is embodied for arrangement at a specific drilling device with a predetermined, supported drilling needle that can be guided along a drill axis and exits from a housing of the drilling device at the front side. In this context, it is provided that the deflector attachment can be arranged at the front side of the drilling device and comprises a deflector housing for guiding the drilling needle which exits from the housing of the drilling device. In this context, the deflector housing in an arrangement of use is curved about a predetermined angle and therefore provides the drilling needle exit axis for the drilling needle which is offset by the predetermined angle in relation to the drill axis of the drilling device.

Herein, all drills that can be elastically bent, i.e., will return after bending into the original shape, are to be understood as "drilling needle". Usually, these are drills whose shaft length is many times larger than the diameter and is approximately in a range of 75:1 (bending radius drilling needle to diameter drilling needle) or larger so that the drill that usually is comprised of a metallic material is elastically bendable. The required bending capability can be enhanced by a suitable material or alloy selection for the drilling needle.

The "specified drilling device" is insofar a "specified device" because the deflector attachment is appropriately configured from the start to be arrangeable or fastenable at the housing of a respective drilling device so that the respective geometries and also fastening elements at least at the deflector attachment are matched with the geometries and optionally, if present, also fastening elements at the housing of the respective drilling device in order to be able to connect the deflector attachment safely and firmly for the intended work to the drilling device.

Correspondingly, "arrangement of use" means also the state in which the deflector attachment and drilling device are coupled to each other ready to operate and the deflector attachment provides for the deflection of the drilling needle about the predetermined angle in order to be able to carry out drilling at a location that is difficult to reach.

Herein, "locations that are difficult to reach" means locations where drilling is to be carried out that an user cannot reach in an ergonomic way easily with a conventional drilling device, for example, in case of trees or wooden poles in the region of the ground level or above head of the user, also, for example, in case of beams of timber frame construction or generally in case of arbitrary situations in building construction or of objects which a user cannot reach easily with a conventional drilling device or drilling resistance measuring device in order to be able to introduce the drilling needle professionally and properly into the object, in particular when the drilling needle is to be introduced in a specified angular position into the object. Thus, for introducing a bore at a right angle, conventional drilling devices or drilling resistance measuring devices must also be positioned at a right angle to the axis of the object or surface of the object. Thus, "locations that are difficult to reach" are located above or below a working range or a working plane, within which a user of a drilling device can professionally and properly carry out drilling at a predetermined angular position, in particular at a right angle, without further auxiliary means in an ergonomic position. A location that is difficult to reach can additionally also be positioned horizontally outside of the working range of a user of a conventional drilling device or drilling resistance measuring device.

In particular, the drilling device at which the arrangement of the deflector attachment according to the invention is provided can be a drilling resistance measuring device which is embodied for carrying out drilling resistance measurements. A drilling resistance measuring device is an apparatus that is created, suitable, and embodied explicitly for drilling resistance measurements.

With the deflector attachment, in an arrangement of use of the deflector attachment at the drilling resistance measuring device, the drilling needle which exits from the housing of the drilling resistance measuring device can be guided in the deflector housing that is curved in the arrangement of use about the predetermined angle and provides a drilling needle exit axis which is offset by a predetermined angle in relation to the predetermined drill axis of the drilling resistance measuring device.

Advantageously, with such a deflector attachment according to the invention a drilling resistance measuring device, even a conventional one, can be retrofitted or converted in order to carry out drilling resistance measurements at locations that are difficult to reach.

Even though it is conceivable that a drilling device or drilling resistance measuring device can be provided permanently with a deflector attachment that is then non-detachably connected to the drilling device/drilling resistance measuring device, it is however advantageous when a deflector attachment according to the invention is detachably arranged at the drilling device/drilling resistance measuring device—and is appropriately configured—so that the deflector attachment, after carrying out drilling at the location that is difficult to reach, can be demounted again in order to be able to use the drilling device/drilling resistance measuring device again for drilling/drilling resistance measurements within the working range (i.e., for locations that are easy to reach) of a user.

For detachable fastening at a drilling device or a drilling resistance measuring device, the deflector attachment, at the end that is facing in the arrangement of use the drilling device or the drilling resistance measuring device, comprises fastening means which are embodied in accordance with the "counterpart". Advantageously, the fastening means at the deflector attachment can be embodied to correspond to the fastening means that are present at or near the needle exit-associated front side of the housing of the predetermined drilling device or the drilling resistance measuring device. Particularly advantageously, the deflector attachment can have a front cover element at which the fastening means are present which correspond with the fastening means at the needle exit-associated front side of the housing of the predetermined drilling device or the drilling resistance measuring device. In this context, "corresponding" means that the fastening means that are present at the two parts to be connected to each other are matched to each other such that they can be brought into engagement with each other such that a securing action of the parts at each other is provided for proper performance of the work.

A further embodiment of the deflector attachment according to the invention provides that the deflector attachment comprises a drilling needle guiding tip at its end which is facing away from the fastening means, i.e., at the end at which the deflected drilling needle exits. Within this drilling needle guiding tip at least one centering element is preferably provided that provides for a centered guiding action of the drilling needle exiting from the deflector attachment in relation to the drilling needle exit axis in order to be able to carry out the intended drilling or drilling resistance measurement exactly at the intended location.

In an embodiment, the deflector housing can be a rigid deflector housing that is curved about the predetermined angle and thus always provides, even in the arrangement of use, the drilling needle exit axis that is offset by the predetermined angle in relation to the drill axis. Rigid deflector housings can be curved differently so that deflector attachments with different angles can be made available.

For guiding the drilling needle in and through the rigid deflector housing, the latter can provide in a further embodiment, at the end that is facing in the arrangement of use the predetermined drilling device or drilling resistance measuring device, a connecting guiding adapter for the drilling needle which comprises a through opening for the drilling needle. The position of the through opening corresponds with the position of the drilling needle exit from the drilling device/drilling resistance measuring device and is aligned with the drill axis so that the drilling needle in the arrangement of use is received exactly in the connecting guiding adapter of the deflector housing from the drilling device/drilling resistance measuring device. The connecting guiding adapter can be held accordingly in a centered connecting holder of the deflector attachment in order to ensure the exact positioning of the through opening in the connecting adapter at the drilling needle exit when the deflector attachment is arranged and fastened in the arrangement of use at the front side of the drilling device/drilling resistance measuring device.

For guiding the drilling needle, rotating in use, within the rigid deflector housing in order to provide the curvature of the drilling needle about the predetermined angle such that it is guided as vibration-free as possible, in an embodiment a curved continuous hose-type guiding element, that is held at least at its two ends by a holding ring, can extend from the connecting holder to an exit opening of the deflector attachment where the drilling needle guiding tip is arranged. The continuous guiding element is embodied with regard to dimensions and material such that the rotating drilling needle is guided through the bend with little clearance. As an alternative to the continuous guiding element, between the connecting holder and the exit opening of the deflector housing several individual guiding or bearing elements can be arranged along a curvature course intended for the drilling needle. The individual guiding or bearing elements are also embodied with regard to dimensions and material such that the rotating drilling needle is guided with little clearance through the bend.

Optionally, for guiding the drilling needle in the deflector attachment, a continuous guiding element can also be combined with individual guiding elements wherein, for example, the individual guiding elements can be arranged for fixation of the position of the continuous guiding element.

In an embodiment as an alternative to the rigid deflector housing of the deflector attachment, the deflector housing can be a bendable deflector housing which, for carrying out drilling/drilling resistance measurement at a location that is difficult to reach, can be bent into the desired curvature in accordance with a predetermined angle and, when not in use, can be bent about an arbitrary angle to a predetermined maximum angle which depends on a type and length of the bendable deflector housing. The bendable deflector housing comprises therefore only in the respective arrangement of use the predetermined angle and can advantageously be bent into different angular positions so that, depending on the position of the location that is difficult to reach, a suitable deflection angle can always be adjusted that enables a drilling action that can be performed at a desired angle, in particular penetrating at a right angle into the test object.

The bendable deflector housing can be formed, for example, by an articulated hose which preferably can be comprised of hose segments that are connected to each other by ball joints. Advantageously, the articulated hose not only can be adjusted at a predetermined angle but can also be arrested or fixed by an integrated mechanical locking action in the bend adjusted according to the predetermined angle. This fixation can be released at any time so that the articulated hose can be bent about a different angle. As an alternative to an articulated hose, a bendable hollow shaft is conceivable as a bendable deflector housing. A bendable hollow shaft comprises one or a plurality of angular position(s) and can comprise at its free end—the end which in the arrangement of use is facing away from the drilling resistance measuring device—a holding sleeve at which the bendable hollow shaft that cannot be fixed in its angular position can be held manually or by means of an additional holding apparatus in order to assume the predetermined angular offset that enables a drilling action at a predetermined angle, in particular penetrating at a right angle into the test object at the location that is difficult to reach.

A further subject matter of the invention is a drilling apparatus for carrying out drilling at locations that are difficult to reach, wherein the drilling apparatus in a first embodiment comprises a drilling device, a drilling needle supported and guided in the drilling device and provided for exit at the front side from the housing of the drilling device in use, and a deflector attachment according to the invention. Of course, the drilling device, as usual, has also a drive unit for the drilling needle. The drilling needle, which is guided in the housing of the drilling device or drilling resistance measuring device along the drill axis to an exit opening at the front side, exits here for carrying out the resistance measurement. According to the invention, the deflector attachment is now arranged at this front side of the housing in order to form the drilling apparatus. In this arrangement, when working with the device, the drilling needle can extend from the exit opening at the front side of the drilling device into and through the deflector attachment. For this purpose, the deflector attachment comprises the deflector housing, which in an arrangement of use is curved about a predetermined angle, for the drilling needle. In this way, a section of the drilling needle exiting from the deflector attachment is guided along the drilling needle exit axis which is offset by the predetermined angle in the arrangement of use in relation to the drill axis of the drilling device. Thus, the drilling device, for example, must not be placed at a right angle against the object in order to carry out a drilling action penetrating at a right angle. The deflector attachment enables in this context positioning of the drilling device in deviation from a right angle arrangement at the object because the distance to a location that is difficult to reach is bridged by the deflector attachment so that the drilling action penetrating at a right angle can be performed by means of the deflector attachment comfortably at the location that is difficult to reach.

In particular, the drilling apparatus according to the invention can be an apparatus for carrying out drilling resistance measurements wherein the drilling device is a drilling resistance measuring device that, in addition to the usual drive unit for the drilling needle, comprises a detection device for detecting the drilling resistance when carrying out a drilling action and a display and/or storage unit for displaying and/or storing the drilling resistance which is detected during the drilling action. This drilling device also comprises a deflector attachment according to the invention which is arranged for deflection of the drilling needle about the predetermined angle at the needle exit-associated front side of the housing of the drilling resistance measuring device.

Moreover, in a further embodiment it is provided that in a drilling apparatus according to the invention the deflector attachment is detachably connected to the housing at the front side of the drilling device or drilling resistance measuring device so that the deflector attachment is reversibly mountable and demountable at any time. Advantageously, in this way the drilling device or drilling resistance measuring device can be operated also without deflector attachment when drilling actions within the working range are to be carried out, or the deflector attachment, when the deflector attachment comprises a rigid deflector housing, can be exchanged, as needed, for example, when due to the position of the location that is difficult to reach a different predetermined angle is required. In this way, many types of drilling devices and drilling resistance measuring devices known in the prior art can be retrofitted or converted with a deflector attachment to a drilling apparatus according to the invention.

In order for the deflector attachment to be detachably fastened at the front side of the drilling device or of the drilling resistance measuring device, corresponding fastening means can be provided which are positioned at the end of the deflector attachment that is facing the drilling device or the drilling resistance measuring device. For example, clips or locking noses can be provided here which are configured such that they can engage cutouts or undercuts which are already present at the housing of the drilling device or of the drilling resistance measuring device. As an alternative thereto, the housing of the drilling device or of the drilling resistance measuring device can also be provided with fastening means which correspond with fastening means at the deflector attachment. For example, for this purpose, a sleeve of plug-in, locking, clamping, screwing or bayonet closure elements can be attached at or near the front side of the housing of the drilling device or of the drilling resistance measuring device and can engage corresponding locking elements as fastening elements of the deflector attachment.

Particularly advantageously, the deflector attachment can comprise, for connection to the housing of the drilling device or of the drilling resistance measuring device, at the corresponding end of the deflector housing a front cover element which corresponds to a front cover of a drilling device or drilling resistance measuring device without deflector attachment in its outer dimensions and with respect to the fastening elements provided thereat. Like a conventional front cover, such a front cover element comprises then, for example, through openings for screws or pins which are aligned with threaded bores at the housing of the drilling device or drilling resistance measuring device so that the deflector attachment, after removal of the front cover, can be fastened in a simple way to the housing by means of the front cover element. In this way, retrofitting or conversion of a conventional drilling device or drilling resistance measuring device or the exchange of different deflector attachments is particularly easy. Advantageously, this attachment ensures an exact positioning of the deflector attachment in relation to the drilling needle exit at the drilling device/drilling resistance measuring device. At the other end, the deflector attachment can comprise a drilling needle guiding tip through which the drilling needle exits, being guided, from of the deflector housing. For this purpose, the drilling needle guiding tip can comprise centering elements for guiding the drilling needle.

In one embodiment of the drilling apparatus according to the invention in which the deflector attachment comprises a rigid deflector housing, the latter can comprise at the end which is facing the drilling device or drilling resistance measuring device additionally a connecting guiding adapter for the drilling needle which is held in a centering connecting holder within the deflector housing. A curved guiding element such as, for example, a flexible guiding hollow shaft, e.g., a braided hose, can extend from this connecting holder to an exit opening of the deflector housing at which the drilling needle guiding tip is arranged. This guiding element can be held at least at the two ends e.g. by means of a holding ring, respectively, and provides a continuous guiding action for deflection of the drilling needle. As an alternative to a continuous guiding element, between the connecting holder and the exit opening of the deflector housing, several individually arranged guiding elements such as, for example, ball bearings, can be provided which are arranged along the intended drilling needle course within the deflector housing at specified spacings (that depend on the number of individual guiding elements) and in predetermined angular position in order to deflect the drilling needle in the intended way, wherein the drilling needle runs essentially free between the individual guiding elements.

A conversion set according to the invention is provided for conversion or retrofitting of drilling devices or drilling resistance measuring devices with a supported and guided drilling needle that exits from the housing of the drilling device or drilling resistance measuring device at the front side for carrying out drilling actions at locations that are difficult to reach. In this context, the conversion set comprises at least two, preferably a plurality of deflector attachments according to the invention which are different with regard to the predetermined angle, which is determined by the deflector attachments of the embodiment with rigid deflector housing. Alternatively or additionally, a conversion set according to the invention can comprise deflector attachments in different lengths wherein also here the deflector attachments of different lengths in case of the rigid deflector housings can be provided with different angles. Moreover, it is provided that the deflector attachments provided in a conversion set according to the invention may differ in addition or alternatively with regard to the fastening elements. By means of the conversion set, not only a matching deflector attachment can be selected for different drilling devices or drilling resistance measuring devices but it can also be selected so as to match with regard to length and/or angle as a function of the position of the location where the drilling action is to be carried out. For forming a drilling apparatus according to the invention, a matching deflector attachment can then be selected and arranged in the arrangement of use at the corresponding drilling device or drilling resistance measuring device for carrying out a drilling action at an intended location outside of the working range.

Compared to a drilling needle of a drilling device or drilling resistance measuring device without deflector attachment, the drilling needle of a drilling device or drilling resistance measuring device according to the invention is extended by the length of the deflector attachment. Moreover, when selecting the drilling needle to be employed, care must be taken that the employed material has a sufficient elastic bending ability.

A drilling apparatus according to the invention can thus be used for drilling at a predetermined location of an object to be tested which is outside of a working range provided for the drilling device, as defined above, in that the drilling apparatus with the deflector attachment is arranged at the intended location such that a section of the drilling needle which exits from the deflector attachment along the drilling needle exit axis is introduced at the intended location in a predetermined angular position, in particular at a right angle in relation to a longitudinal axis of the object to be tested, wherein the deflector attachment deflects the drilling needle, which is guided in the housing of the drilling resistance measuring device along the drill axis, about a predetermined angle.

A method according to the invention for carrying out drilling resistance measurement at locations that are difficult to reach of an object provides therefore the use of a drilling apparatus according to the invention and comprises in a first embodiment the steps:
  arranging and fastening a deflector attachment at the front side of the predetermined drilling device or drilling resistance measuring device, preferably detachable fastening by engaging the fasting means of the deflector attachment with the drilling device or drilling resistance measuring device or with fastening means of the drilling device or drilling resistance measuring device;
  exchanging the drilling needle of the drilling device or drilling resistance measuring device for a drilling needle which is extended by the length of the deflector attachment;
  placing the drilling apparatus with the deflector attachment against the predetermined location of the object so that the drilling needle exit axis is arranged in the predetermined angular position, in particular at a right angle in relation to a longitudinal axis or a surface plane; and
  carrying out the drilling action or drilling resistance measurement by allowing a section of the drilling needle that exits from the deflector attachment along the drilling needle exit axis to penetrate at the intended location, wherein the drilling needle is deflected about the predetermined angle in relation to the drill axis by the deflector attachment.

A further embodiment of the method according to the invention provides for selecting and determining the deflector attachment prior to arranging and fastening the deflector attachment. In this context, the selection can be realized, for example, from the set which is provided with two or more deflector attachments and which is combined in the conversion set according to the invention. The determination comprises in this context determining an angle which is suitable for working in the working range and thus forms the "predetermined angle", and in addition it also includes determining a suitable length of the deflector attachment and/or identifying and determining suitable fastening means; always taking into consideration indeed the position of the predetermined location (in relation to the working range) as well as taking into consideration the drilling device or drilling resistance measuring device.

Alternatively or additionally, the method according to the invention, prior to arranging and fastening the deflector attachment, can comprise the removal or release of another deflector attachment or a front cover which are arranged at the predetermined drilling device or the predetermined drilling resistance measuring device.

Finally, when using a deflector attachment with a bendable deflector housing for placing the drilling device with the deflector attachment against the predetermined location of the object so that the drilling needle exit axis of the deflector attachment is arranged in the predetermined angular position, in particular at a right angle in relation to a longitudinal axis or a surface plane, the step is provided that the bendable deflector housing is bent for adjusting the angle that is predetermined by the position of the predetermined location in relation to the working range.

Further embodiments as well as some of the advantages which are associated with these and further embodiments will become clear and more easily understood by means of the following detailed description with reference to the accompanying drawings. Objects or parts thereof which are substantially identical or similar can be provided with the same reference characters. The Figures are only a schematic representation of embodiments of the invention.

BRIEF DESCRIPTION OF THE DRAWINGS

It is shown in.

DESCRIPTION OF PREFERRED EMBODIMENTS

The apparatus according to the invention concerns a deflector attachment 1 as it is illustrated in an exemplary fashion in different embodiments in the FIGS. 1 to 10. With this deflector attachment 1, the conventional drilling device 111 or the drilling resistance measuring device 11 can be converted in order to be able to carry out drilling or drilling resistance measurements in an ergonomic working position of the user even at locations that are difficult to reach, as in the region of the ground level, for example, at trees or wooden poles or above head, for example, at beams of a timber frame construction. Even below the ground level, for example, in case of exposed poles, drilling or resistance measurements can be carried out comfortably with the drilling apparatus 10 according to the invention, which is comprised of a drilling device 111 or drilling resistance measuring device 11 and a deflector attachment 1.

Figure 3:
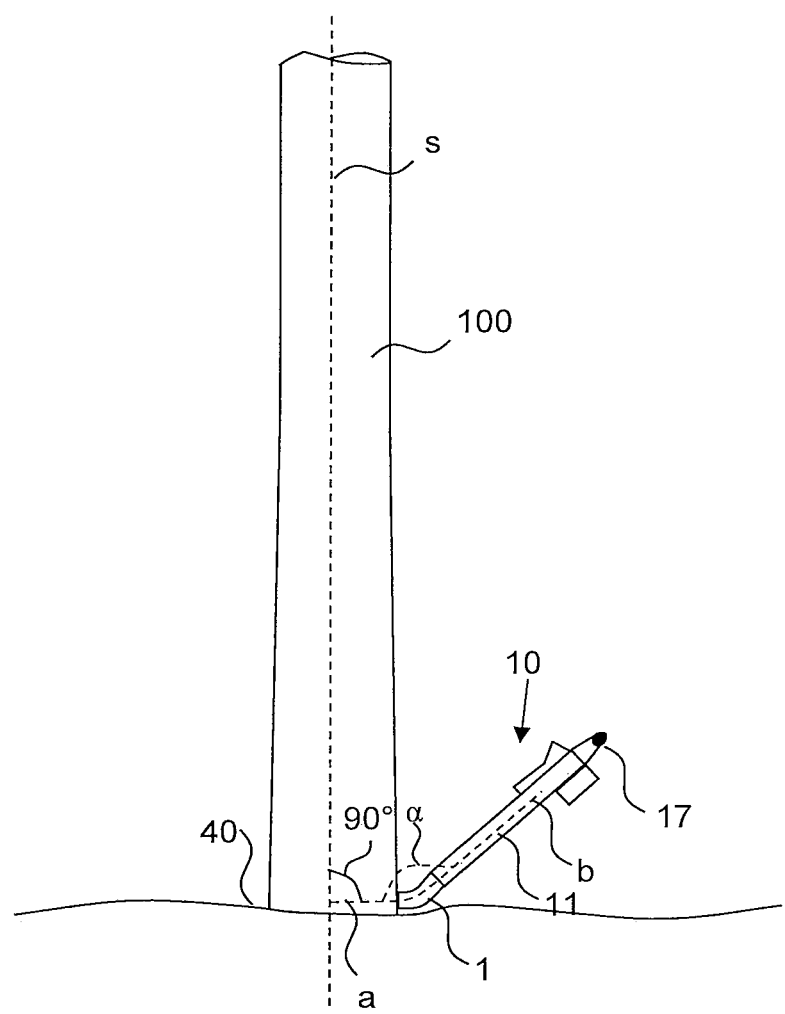
FIG. 3 a schematic side view of a drilling resistance measuring apparatus according to the invention when carrying out a drilling resistance measurement at a location that is difficult to reach in the region of the ground level.
Figure 5:
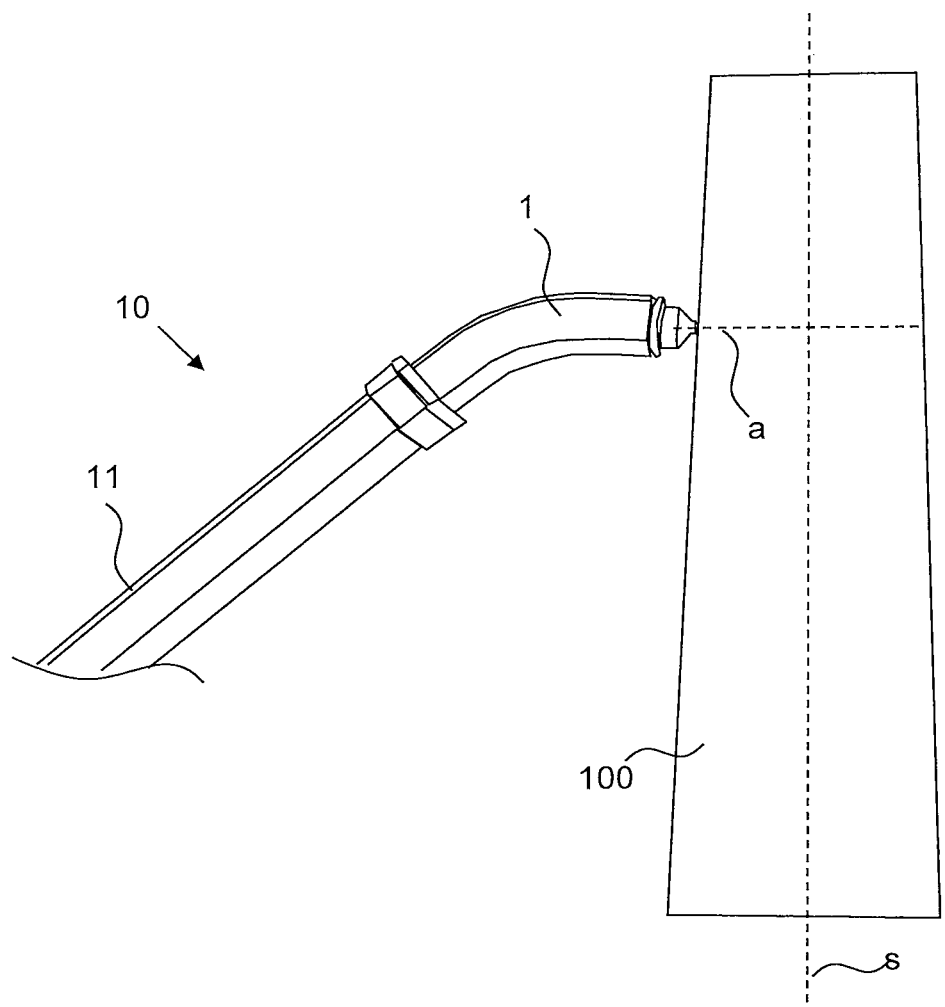
FIG. 5 a schematic side view of a drilling resistance measuring apparatus according to the invention when carrying out a drilling resistance measurement at a location that is difficult to reach above head.

In this context, a drilling action that is at a right angle or approximately at a right angle to the pole or tree or beam axis, as illustrated in FIGS. 3 and 5, can also be carried out without problem. Of course, also measuring drilling actions at an angle deviating from a right angle can be carried out, if this appears to be expedient, with the drilling apparatus 10. For example, when the deflector attachment 1 provides for a deflection of the drilling needle 19 by a predetermined fixedly adjusted angle, the drilling resistance measuring device 11 could be provided with a bubble level in accordance with a mason's level for alignment in horizontal or vertical position so that a measuring drilling action can be carried out exactly at the predetermined fixedly adjusted angle.

In relation to the drilling resistance measurements for determining the inner state of an object 100, the measuring drilling action that is performed substantially at a right angle is however preferred because here the position of possible defects such as decay or the like in the interior can be more simply determined even without complex evaluation.

Figure 1:
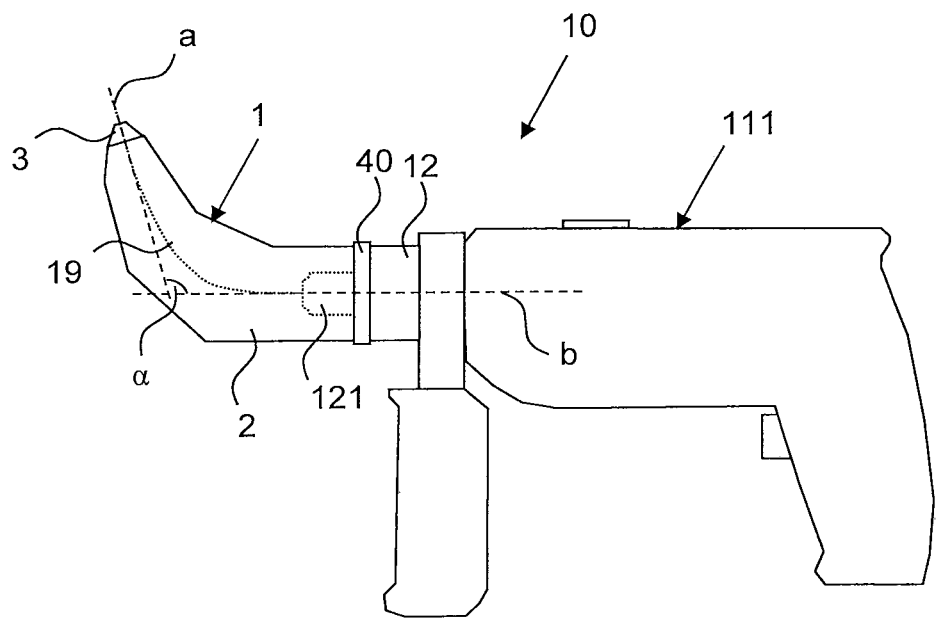
FIG. 1 a schematic side view of a drilling apparatus according to the invention with drilling device and deflector attachment with rigid deflector housing.
Figure 2:
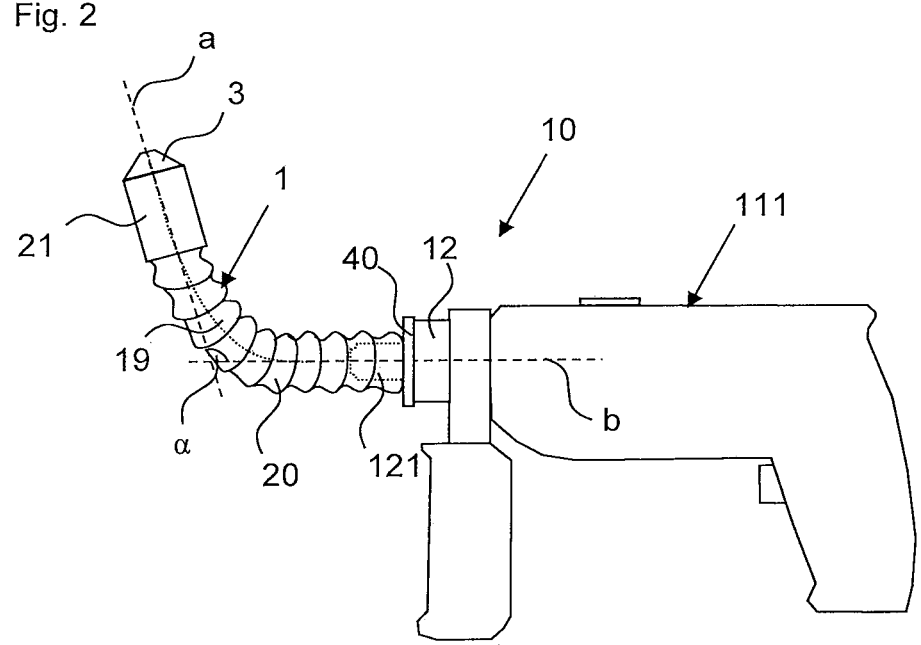
FIG. 2 a schematic side view of a drilling apparatus according to the invention with drilling device and deflector attachment with bendable deflector housing.

FIG. 1 and FIG. 2 show respectively a drilling apparatus 10 according to the invention for carrying out drilling at a location that is difficult to reach of an object that is comprised of wood, for example. The drilling apparatus 10 comprises in this example a drilling device 111 that, at its front side, comprises a housing part 12 in which the drilling needle 19, illustrated in dotted line, is supported and guided in a chuck 121, also illustrated in dotted line and projecting from the housing part 12 in the illustrated example, and is coupled with a drive unit of the drilling device 11 that is not illustrated. A detailed illustration of the drilling device 111 is not provided because, in principle, any commercially available drilling device can be retrofitted with a deflector attachment 1 according to the invention in order to carry out drilling at locations that are inaccessible, provided the employed drill is a bendable drilling needle 19. The deflector attachment 1 which is arranged at the front side of the drilling device 111 enables that the drilling needle 19, which is guided out of the housing 12 of the drilling device 111 along a drill axis b, is deflected about the predetermined angle α, which in FIG. 1 is preset by the rigid deflector housing 2 of the deflector attachment 1 and in FIG. 2 is adjusted by the bendable deflector housing 20, so that the drilling needle 19 can exit along a drilling needle exit axis a from the drilling needle guiding tip 3 of the deflector attachment 1 which is offset by the angle α relative to the drill axis b. The deflector attachment 1 in this context is attached by means of a schematically illustrated fastening element 40 at the housing 12 of the drilling device 111, respectively. Different embodiments of possible fastening elements will be explained in the following. The bendable deflector housing 20 in FIG. 2 is formed by an articulated hose with an exit sleeve 21 that is adjoined by the drilling needle guiding tip 3.

Figure 4:
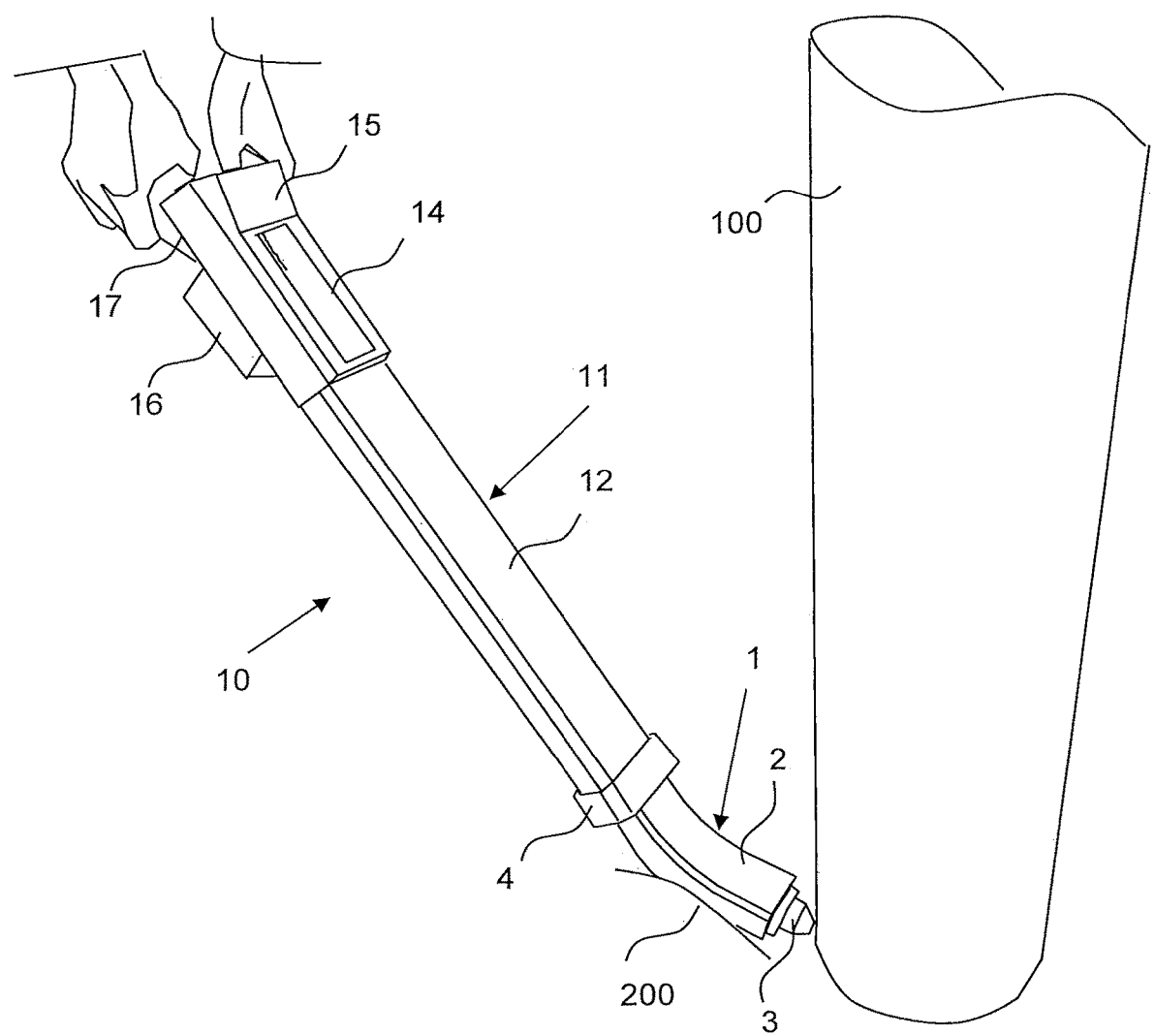
FIG. 4 a perspective view of a drilling resistance measuring apparatus according to the invention when carrying out a drilling resistance measurement at a location that is difficult to reach in the region of the ground level.

FIG. 3 shows schematically and FIG. 4 in more detail a drilling apparatus 10 according to the invention for carrying out drilling resistance measurements at a location, difficult to reach, of a tree or pole 100, here in the region of the ground level 200 (earth mound). FIG. 5 shows the use of the drilling apparatus 10 for carrying out an overhead measurement.

The drilling apparatus 10 comprises in this example a drilling resistance measuring device 11 which in a conventional way comprises a housing 12 and a detection device for detecting the drilling resistance when carrying out a drilling resistance measurement. A drilling needle 19 (compare FIG. 7 and FIG. 8) is supported and guided in the housing 12 and coupled with a drive unit 16. A detailed illustration of the drilling resistance measuring device 11 is not provided herein because, in principle, any commercially available drilling resistance measuring device can be retrofitted with a deflector attachment 1 according to the invention in order to be able to carry out drilling resistance measurements at inaccessible locations. The deflector attachment 1 which is arranged at the front side exit opening of the drilling resistance measuring device 11 makes it possible that the drilling needle 19, which is guided in the housing 12 of the drilling resistance measuring device 11 along a drill axis b, is deflected such that it can be introduced at a right angle to the trunk or pole axis s.

In the examples of the deflector attachment 1 illustrated in FIGS. 1 and 3 to 6, the deflection of the drilling needle 19 by a predetermined fixed angle α is determined by a rigid curved deflector housing 2. Angle α is formed between the drilling needle exit axis a, which is defined by a section of the drilling needle 19 with the drilling needle tip 19' exiting from the deflector attachment 1, and the drill axis b of the drilling device 111 or of the drilling resistance measuring device 11.

Figure 6:
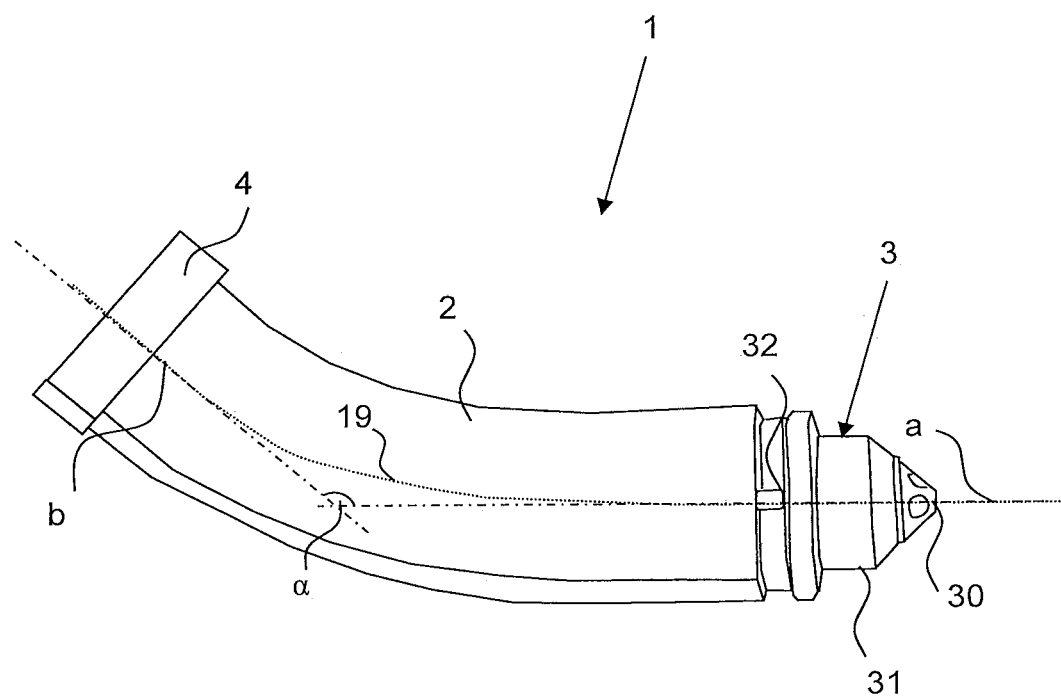
FIG. 6 a schematic side view of a deflector attachment of an embodiment according to the invention with rigid deflector housing.

For arrangement of the deflector attachment 1 at the front side exit opening of the drilling resistance measuring device 11, the deflector attachment 1, as illustrated in particular in FIGS. 4 and 6, is provided at the end facing the drilling resistance measuring device 11 with a front cover element 4. The latter is embodied in regard to the dimensions and the fastening elements in accordance with the front cover of the drilling resistance measuring device 11 without deflector attachment 1 so that, for conversion of a conventional drilling resistance measuring device 11, its front cover can simply be removed and the deflector attachment 1 with the front cover element 4 fastened to the housing 12 of the drilling resistance measuring device 11. For this purpose, releasable plug-in or locking mechanisms can be provided, but screw connections can be employed also. The front cover element 4 which is illustrated in the present example has in accordance with the housing 12 of the drilling resistance measuring device 11 a rectangular cross section. Of course, also other cross section shapes are conceivable, and fastening without front cover element 4 is also conceivable, wherein the deflector housing can be fastened at the front side of the drilling device/drilling resistance measuring device without the front cover thereof having to be removed.

Figure 7:
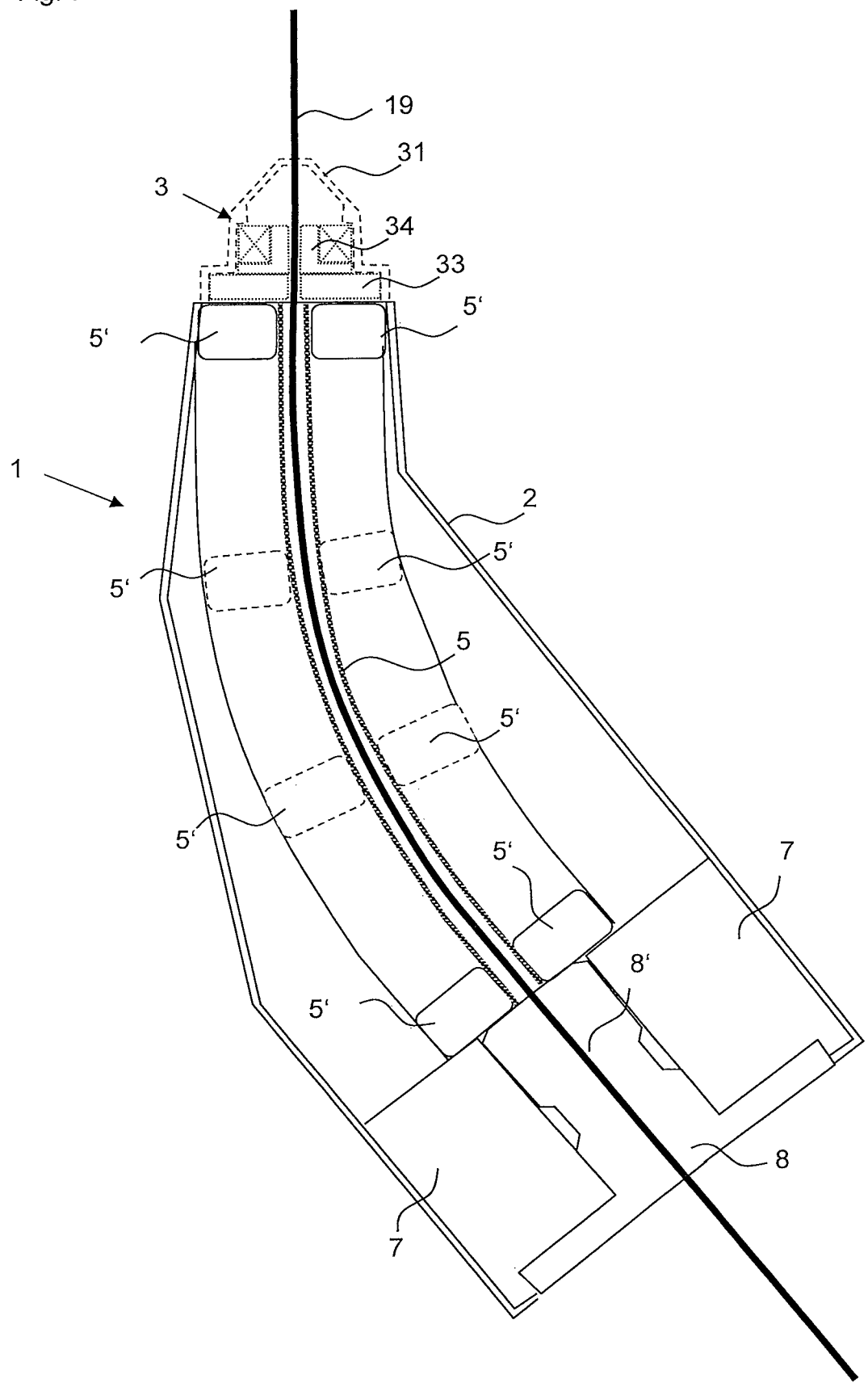
FIG. 7 a longitudinal section view of a deflector attachment of an embodiment according to the invention with rigid deflector housing.

At the other end of the deflector attachment 1 where the drilling needle 19 with the drilling needle tip 19' exits, the deflector attachment 1 comprises, as can be seen in FIGS. 1, 2 and 4 to 8, a drilling needle guiding tip 3 whose housing 31 tapers away from a connecting flange section in a conical shape to a drilling needle exit opening 30. In this guiding tip housing 31 corresponding centering elements ensure a centered guided exit of the drilling needle 19. In FIG. 7, in the housing 31 of the drilling needle guiding tip 3, for example, a centering disc 33 and a rotatably supported guiding sleeve 34 are indicated as centering elements. The further element 32, which is illustrated in FIG. 6 neighboring the drilling needle guiding tip 3, is a safety switch by means of which an accidental exit of the drilling needle is prevented. This safety switch 32 is actuated in order to make ready a drilling resistance measuring apparatus 10 according to the invention.

Furthermore, FIG. 7 shows in section illustration an exemplary embodiment of a deflector attachment 1 which comprises a deflector housing 2 for deflecting the drilling needle 19 which is advanced from the drilling device or drilling resistance measuring device not illustrated here. In the deflector housing 2, at the end which is facing the drilling device or drilling resistance measuring device, a connecting guiding adapter 8 with a through opening 8' for the drilling needle 19 is provided and accommodates in a centered and guided fashion the drilling needle 19 coming from the drilling device or the drilling resistance measuring device. The connecting guiding adapter 8 itself is held in a centering connecting holder 7. Between the connecting holder 7 and the exit opening of the deflector housing 2 at which the drilling needle guiding tip 3 is arranged, a curved guiding element 5 in the form of a guiding hollow shaft is extending which is held at both ends in a holding ring, respectively. At the same time, the alternative guiding of the drilling needle 19 by means of individual guiding elements 5', for example, ball bearings or other bearings, is indicated by dashed lines in the same FIG. 7, wherein—different from the illustration in FIG. 7—a continuous guiding hollow shaft 5 is not required. In the illustrated example, the four individual guide bearings 5' are arranged uniformly distributed along the intended deflection path for the drilling needle 19 so that two of the guide bearings 5' are arranged, corresponding to the holding rings in the alternative variant with the continuous guiding shaft 5, at the exit opening to the guiding tip 3 and at the connecting holder 7 while a third and a fourth guide bearing 5' are arranged therebetween about the apex of the curvature. In an embodiment with three guide bearings, the central guide bearing can support and guide the drilling needle at the apex of the curvature.

The illustration of housing structures and elements which are required for arranging the guide bearings 5' is not provided. Bearing seats for the guide bearings 5' can be embodied in the conventional way. In deviation from the example illustrated in FIG. 7, more than four guide bearings for guiding the deflection of the drilling needle between the exit opening and the connecting holder can be arranged also. Preferably, the guide bearings are arranged at uniform spacings relative to each other, wherein the spacing depends on the number of employed guide bearings. In this context, the respective angle position of the guide bearings depends on the respective position along the intended drilling needle course.

Since moreover the drilling needle 19 is guided in a centered fashion in the connecting adapter 8 as well as in the drilling needle guiding tip 3, the two guide bearings 5', which are arranged corresponding to the position of the holding rings adjacent to the connecting holder 7 that surrounds the connecting adapter 8 and to the guide tip 3, can be eliminated, as needed.

Optionally also both variants, continuous guiding element 5 and individual guiding elements 5', can be used in combination.

Figure 8:
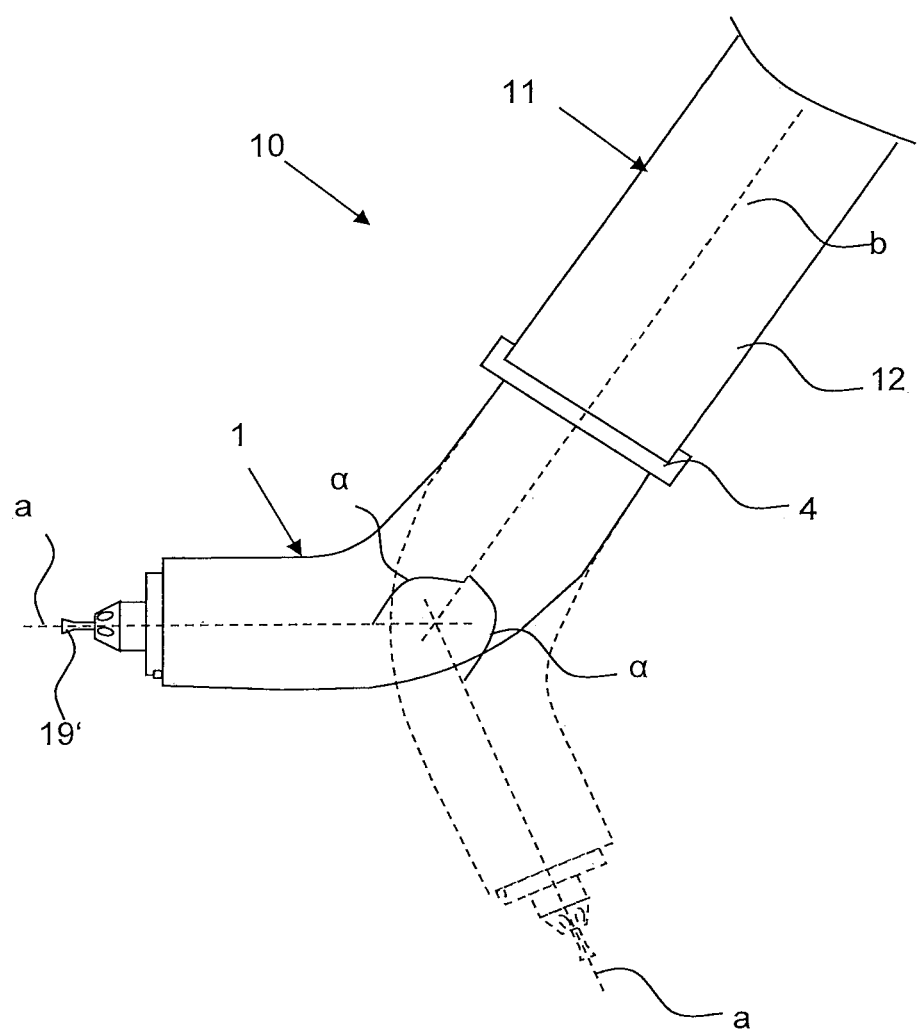
FIG. 8 a detail side view of a drilling resistance measuring apparatus according to the invention with different positions of a deflector attachment with rigid deflector housing and predetermined angle.

In FIG. 8, it is illustrated that a deflector attachment 1 can be arranged in different direction at a drilling resistance measuring device 11. This is relevant insofar as, for carrying out the measurements with the drilling apparatus 10, the display apparatus 14 of the drilling resistance measuring device 11 (compare FIG. 4) should be easily readable and the actuation element 15 easily accessible. Depending on the position of the location that is difficult to reach, the deflector attachment 1 can thus be mounted in a position that is more beneficial therefor. The number of possible mounting positions depends primarily on the cross section shape of the housing 12 of the drilling resistance measuring device 11: In the present example, the housing 12 has a rectangular cross section so that for the deflector attachment 1, as shown in FIG. 8, two possible mounting positions are provided.

Not illustrated, but easily transferable, are embodiments in which the housing of the drilling resistance measuring device, for example, has a square cross section with therefore four possible mounting positions, or optionally also a round cross section which—depending on the fastening mechanism—enables even an arbitrary mounting position of a deflector attachment. As illustrated, for example, in FIG. 4, the fixed angle of the deflector housing 2 can be selected such that the apparatus 10 can be placed comfortably at an inaccessible location in the region of the ground level, even if there is an earth mound 200, by a user who guides the apparatus 10 at the handles 17 of the drilling resistance measuring device 11.

As a conversion set, without problem a plurality of deflector attachments for a drilling resistance measuring device 11 can be provided whose deflector housings have curvatures with different angles $\alpha$ so that, depending on the position of the location that is difficult to reach, a suitable deflector attachment can be selected. For a comfortable drilling resistance measurement at an object in the region of the ground level, an angle $\alpha$ of 45° is expedient as a result of the typical length of the drilling resistance measuring device wherein the user, without having to bend down, can arrange the drilling needle exit opening at the trunk or pole at the ground level in order to perform here a substantially rectangular measurement in relation to the trunk/pole axis. A conversion set can however also have deflector attachments whose rigid housing comprises angles deviating from 45°, for example, 15°, 30°, 75° or 90°, or other angles. In addition, a conversion set can contain deflector attachment sets of different length in order to be able to bridge also different distances to the locations intended for drilling. Finally, a conversion set can also comprise deflector attachments which differ with regard to the fastening elements so that different drilling devices and drilling resistance measuring devices can be converted.

Aside from arranging the deflector attachment 1 at the drilling resistance measuring device 11, the drilling needle 19 must be exchanged for conversion because, for the drilling apparatus 10 with the deflector attachment 1, a drilling needle 19 is required that is extended by the length of the deflector attachment 1 in order to be able to carry out the drilling resistance measurement. When converting a drilling resistance measuring device 11, therefore first the old drilling needle is removed and then the front cover of the drilling resistance device 11 can be demounted. At the correspondingly accessible fastening locations, the deflector attachment with the front cover element 4 is fastened whereupon the extended drilling needle 19 can be inserted.

The length of the extended cylindrical drilling needle 19 is thus longer, in accordance with the sections along the axes a and b, than the length of a conventional drilling needle which is already multiple times larger than its diameter that is typically in the range of 0.5 to 2.5 mm, preferably 1.0 mm to 1.5 mm, and as such is also used for an extended drilling needle 19. A preferred drilling needle shape is described in DE 10 2009 013 069 A1 in which the cylindrical needle shaft transitions with a wedge section into a sharp and smooth cutting edge so that the needle can rotate uniformly and displaced material can be pushed in the direction of the needle shaft in order to avoid undesirable edges at which the material could get caught. The drilling needle tip is not rotation-symmetrical but comprises different shapes in two symmetry planes that are perpendicular to each other: In the first symmetry plane relative to a central axis of rotation of the needle, the needle tip has a cutting edge with a width that is larger than a diameter of the cylindrical needle shaft wherein a transition from the needle shaft along the wedge section to the two ends of the cutting edge—the two "flanks" at the needle head—extends with a uniform curvature. In the second symmetry plane relative to the central axis of rotation, which extends orthogonally to the first symmetry plane and through the central axis of rotation, the wedge section has a reduced slant relative to the central axis of rotation compared to the cutting edge that ends at a ridge. The cutting edge of the drilling needle tip 19' comprises in this context— as a function of the needle shaft diameter—preferably a width in a range of 0.8 to 4.0 mm, preferably of 1.0 mm to 2.0 mm.

As an alternative to the embodiment of the deflector attachment 1, described in connection with FIGS. 1 and 3 to 8, with a rigid deflector housing 2 as the deflector guiding apparatus with a fixed predefined angle α, according to the invention also embodiments of the deflector attachment 1 with bendable envelope apparatus 20, 22 as deflector housing are provided which enable an adjustment of an arbitrary angle α within predefined limits. The predefined limits are determined by a maximum angle of the bendable housing 20, 22 which depends on the type and length of the respective housing 20, 22. The drilling needle 19, on the other hand, due to the minimal diameter in comparison to its length can be strongly bent arbitrarily. This can be assisted by a suitable material selection.

Figure 9:
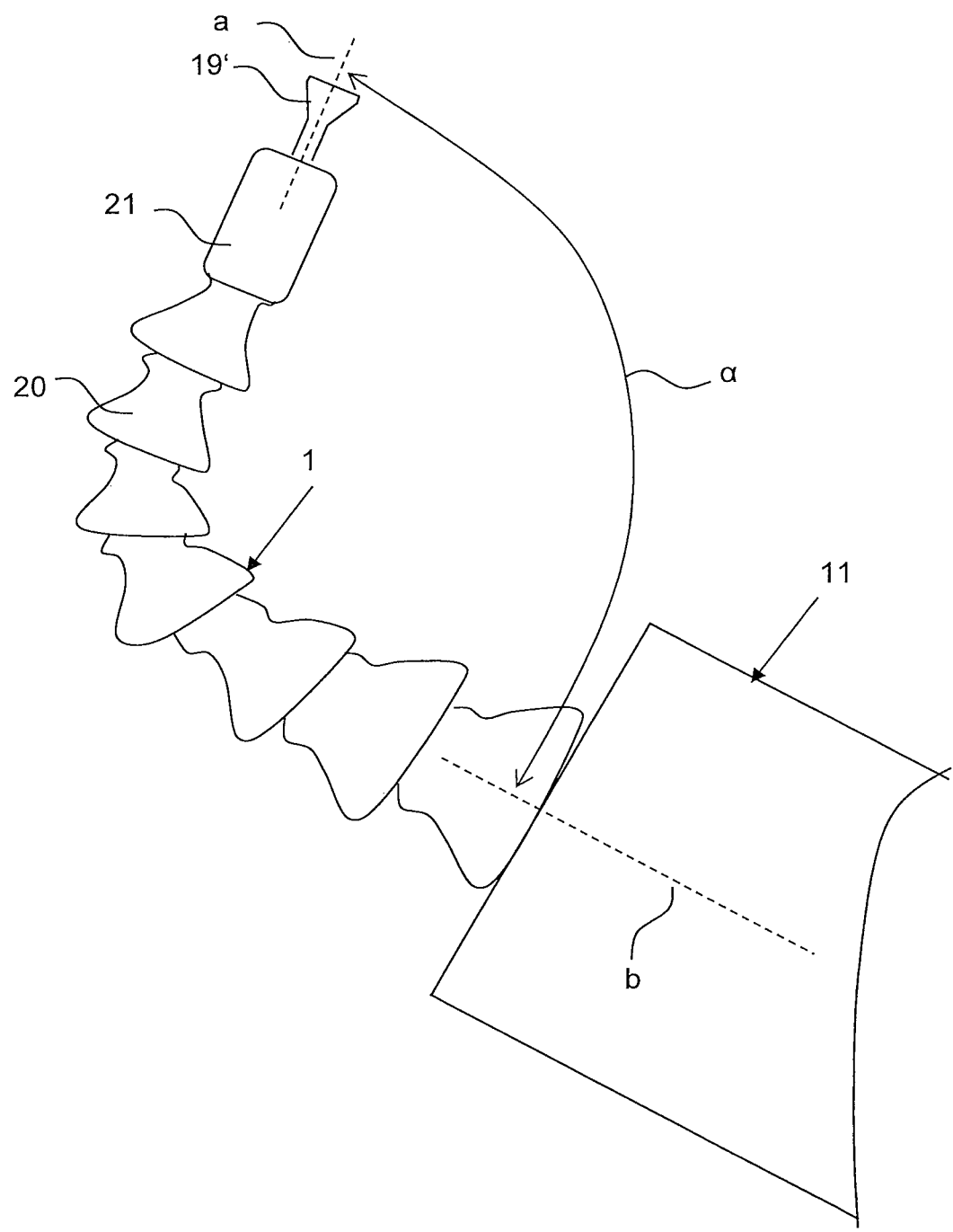
FIG. 9 a schematic side view of a drilling resistance measuring apparatus according to the invention with a deflector attachment with bendable deflector housing with adjustable and securable angle.
Figure 10:
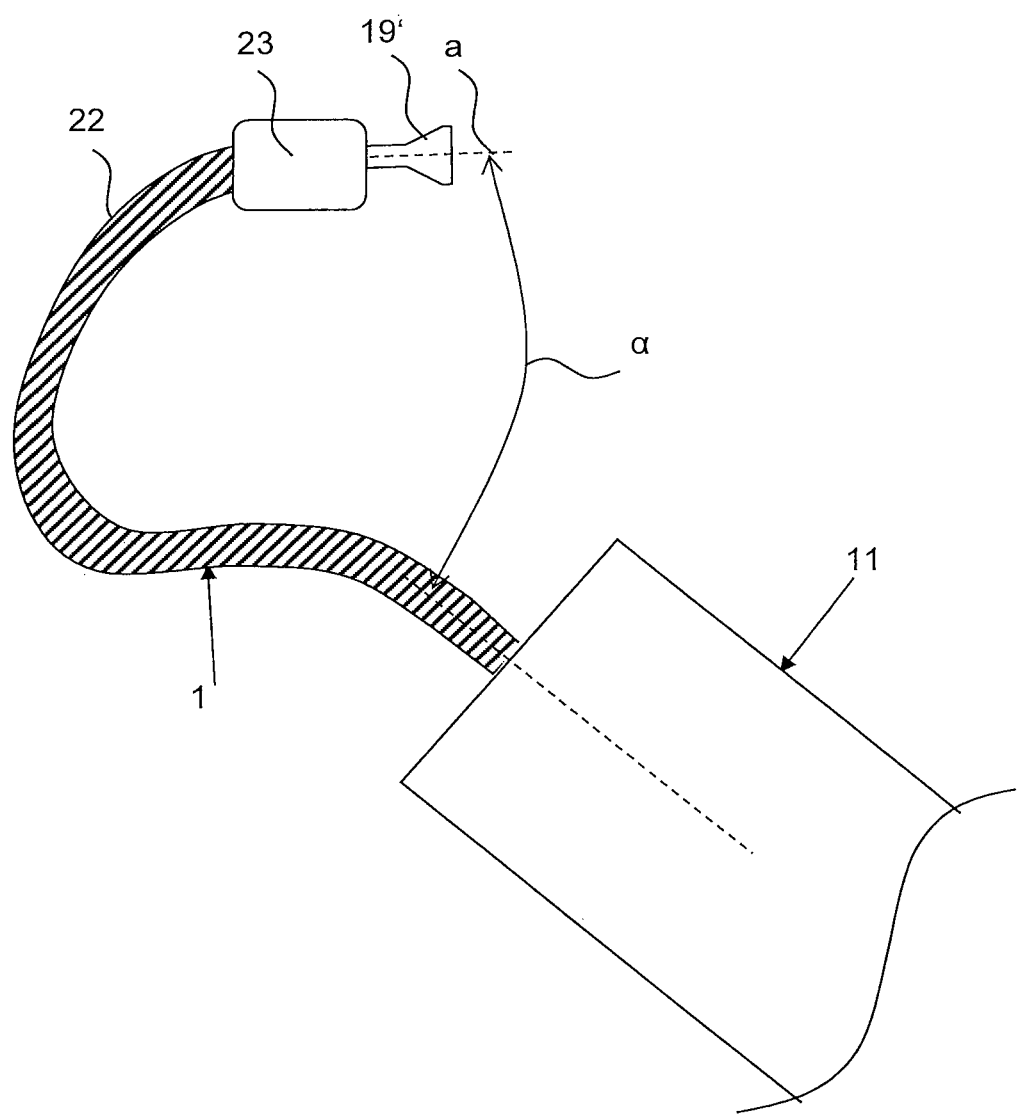
FIG. 10 a schematic side view of a drilling resistance measuring apparatus according to the invention with a deflector attachment with bendable deflector housing on the basis of a flexible hollow shaft with adjustable angle.

As examples for this, in FIGS. 2 and 9 an articulated hose 20 as a bendable deflector housing of the deflector attachment 1 and in FIG. 10 a flexible hollow shaft 22 as a bendable deflector housing of the deflector attachment 1 are illustrated. The articulated hose 20 is comprised of hose segments that are connected to each other by ball joints that enable bending about an arbitrary angle α. The articulated hose 20 enables in addition a fixation of this adjusted angle α which however can be released again so that the articulated hose 20 can be adjusted to a different angle α. The drilling needle exit sleeve 21 provides in this context a centered guiding action of the section of the drilling needle 19 (that extends through the articulated hose 20) with the drilling needle tip 19'. Different from the illustration, here also a guiding tip 3 can be provided alternatively or additionally, as in the above described embodiments with the deflector housing 2.

In a similar way, the drilling needle 19 extends through the bendable hollow shaft 22 which is constructed of one or a plurality of wound layers. Optionally, the outermost wound layer can be enclosed by an elastic protective sleeve. Since the bendable hollow shaft 22 cannot be secured in an adjusted angle α, at the free end of the bendable hollow shaft 22 a sleeve 23 is provided that not only serves as a centering guiding apparatus for the exiting drilling needle 19 but also as a holding apparatus. The drilling needle exit can thus be manually guided and the angle α can be manually adjusted.

Even though this is not illustrated in FIGS. 9 and 10, here also the deflector attachment 1 can comprise, for connection with the housing 12 of the drilling resistance measuring device 11, a front cover element 4 that for conversion is arranged at the front side exit opening of the drilling resistance measuring device 11 in place of the front cover. Alternatively, the deflector attachment however can also comprise fastening elements without a special front cover element in order to fasten the deflector attachment without removal of housing parts of the drilling device at the front side thereof.

Figure 11:
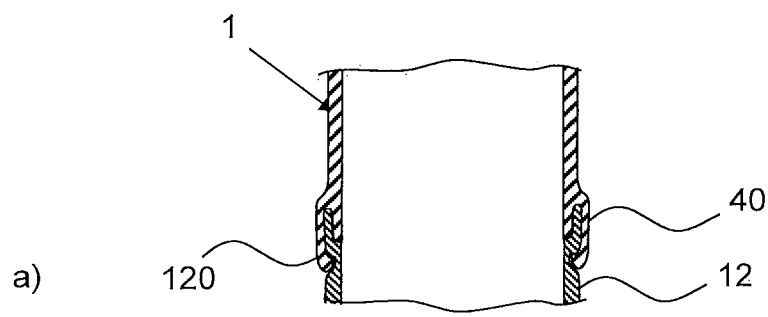
FIG. 11 schematic illustrations a, b, c of different fastening elements at deflector attachment and housing of the drilling device in section views and plan view.
Figure 11:
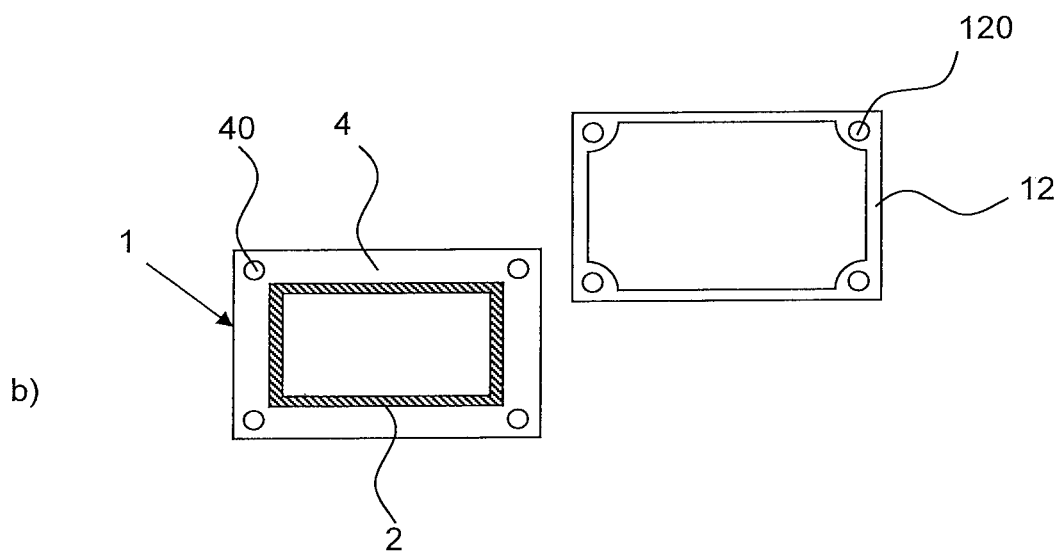

In FIG. 11, three examples a, b, and c for different fastening variants of a deflector attachment 1 at a drilling device or drilling resistance measuring device are illustrated. In a), as a fastening variant, a plug-in or locking closure is schematically shown in which an end section of the deflector attachment 1, facing the drilling device or drilling resistance measuring device, not illustrated, and the housing 12 of the drilling device comprise correspondingly shaped locking elements 40, 120 as fastening elements. In b), in plan view the deflector attachment 1 and, offset thereto, the front side of the housing 12 with rectangular cross section of a drilling device or drilling resistance measuring device can be seen from which a front cover has been removed. The deflector attachment 1 in b) comprises a front cover element 4 wherein the deflector housing 2, which would extend out of the drawing plane, has been illustrated for ease of illustration in section view. The front cover element 4 corresponds in its shape and the dimensions to the removed front cover and comprises through openings 40 as fastening elements which, when placing the deflector attachment 1 against the housing 12, are aligned with the receiving bores 120 provided thereat as corresponding fastening elements so that in this example the deflector attachment 1 can be fastened by means of screws or pins which are inserted through the then aligned through openings 40 and receiving bores 120. In c), an exemplary variant is illustrated in which the deflector attachment 1 comprises, at the end facing the housing 12, a thread 40 as fastening element that can be brought into engagement with the corresponding counter thread 120 at the housing 12.

The examples illustrated in FIG. 11 are however not to be understood in any way as limiting—instead, as fastening elements, all conceivable clamping, plug-in, locking, screwing or bayonet closures etc. are to be encompassed with which a deflector attachment according to the invention— with or without front cover element—can be detachably fastened at a drilling device or drilling resistance measuring device or its housing with or without front cover. As the case may be, the selection of the suitable fastening elements may be limited by a shape of the housing and the, as the case may be, corresponding shape of the deflector housing or of the front cover element. For example, a bayonet or screw closure can be realized only for circular round cross sections. As the case may be, the housing of a drilling device or drilling resistance measuring device can also be supplemented with fastening elements such as receptacles or locking cutouts and other suitable elements in order to be able to be retrofitted with a deflector attachment according to the invention.

It is primarily provided that, for forming a drilling apparatus for drilling or drilling resistance measurement at locations that are difficult to reach, a deflector attachment according to the invention can be reversibly connected, detached, and exchanged for retrofitting or conversion at the front side exit opening of the drilling device or drilling resistance measuring device in order to be able to cover thus a broadest pallet of use with a drilling resistance measuring device, for example, in that also differently angled attachments can be employed and the drilling resistance measuring device can be used without deflector attachment. However, it is also conceivable that a drilling apparatus according to the invention for carrying out a drilling action or drilling resistance measurement at a location that is difficult to reach is embodied as a drilling device or drilling resistance measuring device with deflector attachment that is non-detachable or not exchangeable. In such a case, the variant with a bendable deflector housing of an articulated hose or a bendable hollow shaft or corresponding apparatus is expedient.

Moreover, a device according to the invention can be furnished with elements that assist in or facilitate carrying, erecting or positioning, in particular in case of overhead measurements or in the embodiments with bendable deflector guiding apparatus, primarily with the bendable hollow shaft that cannot be arrested at a predetermined angle but requires an additional guiding of the exit sleeve which is realized either manually or requires additional holder. In addition to the handles 17 illustrated in FIGS. 3 and 4, an apparatus according to the invention can be placed, for example, with a stand near the location that is difficult to reach so that the bendable deflector guiding apparatus can be adjusted or guided comfortably by hand. Conversely, the bendable deflector guiding apparatus at the exit sleeve, for example, with a sleeve or a clip could be placed against the object so that the drilling resistance measuring device of the apparatus according to the invention can be held. Other concepts can provide carrying belts or support cushions in order to be able to carry the drilling resistance measuring device of the apparatus according to the invention like a backpack on the back or across a shoulder at the side or rest it on a shoulder and to thus have the hands free in order to adjust and/or guide the bendable deflector guiding apparatus. It is noted that the embodiments which have been shown with the aid of the examples with a drilling resistance measuring apparatus can also be transferred onto a drilling apparatus which is not embodied for carrying out resistance measurements but only for introducing bores, and vice versa.

LIST OF REFERENCE CHARACTERS 1 deflector attachment
2 rigid deflector housing
20 articulated hose as bendable deflector housing
21 exit sleeve
22 bendable shaft as bendable deflector housing
23 holder sleeve
3, 30, 31 guiding tip, drilling needle exit opening, housing
32, 33, 34 safety switch, centering disc, centering sleeve
4 front cover element
40 fastening means (through openings, locking elements), deflector attachment
5, 5' continuous individual guiding element
7 connecting holder
8, 8' connecting guiding adapter, through opening
10 drilling apparatus/drilling resistance measuring apparatus
11, 111 drilling resistance measuring device, drilling device
12 housing of a drilling resistance measuring device/drilling device
120 fastening means housing drilling resistance measuring device/drilling device
121 chuck
14 display device
15 actuating element
16 drive unit
17 handle
19, 19' drilling needle, drilling needle tip
200 ground level, earth mound
100 pole/tree
a drilling needle exit axis of the deflector attachment
b drill axis of the drilling device/drilling resistance measuring device
s axis pole/tree
α angle between a and b

What is claimed is:

1. A drilling apparatus (10) comprising:
   a drilling device (111) or a drilling resistance measuring device (11);
   a drilling needle (19) supported and guided along a drill axis (b) in the drilling device (111) or the drilling resistance measuring device (11), the drilling needle (19) exiting from a front side of a device housing (12) of the drilling device (111) or of the drilling resistance measuring device (11);
   a deflector attachment (1) arranged at the front side of the device housing (12);
   the deflector attachment (1) comprising a deflector housing (2, 20, 22) configured to guide the drilling needle (19), wherein the deflector housing (2, 20, 22), in an arrangement of use, is curved about a predetermined angle (α);
   wherein a section of the drilling needle (19) exiting from the deflector attachment (1) is guided along a drilling needle exit axis (a) of the deflector attachment (1), wherein the drilling needle exit axis (a) of the deflector attachment (1) is offset, in the arrangement of use, by the predetermined angle (α) in relation to the drill axis (b);
   wherein the deflector housing is a rigid deflector housing (2) comprising a curvature about the predetermined angle (α);
   wherein the deflector attachment (1) comprises an adapter (8) arranged at a first end of the deflector attachment (1), the first end facing the drilling device (111) or the drilling resistance measuring device (11), in the rigid deflector housing (2) and configured to guide the drilling needle (19), wherein the deflector attachment (1) further comprises a holder (7) arranged at the first end in the rigid deflector housing (2), wherein the holder (7) holds and centers the adapter (8).

2. The drilling apparatus (10) according to claim 1, wherein the deflector attachment (1) further comprises a second end oppositely arranged to the first end, wherein the first end comprises first fastening means (40), wherein the device housing (12) comprises second fastening means (120) at or near the front side, wherein the first fastening means (40) correspond with the second fastening means (120), wherein the deflector attachment (1) is connected detachably at the front side to the device housing (12) by the first and second fastening means (40, 120) engaging each other.

3. The drilling apparatus (10) according to claim 2, wherein the deflector attachment (1) comprises a front cover element (4) arranged at the first end, wherein the first fastening means (40) are provided at the front cover element (4), wherein the front cover element (4) comprises dimensions configured to correspond to the dimensions of the device housing (12) at the front side.

4. The drilling apparatus (10) according to claim 1, wherein the deflector attachment (1) comprises a drilling needle guiding tip (3) at a second end of the deflector attachment (1).

5. The drilling apparatus (10) according to claim 4, wherein the drilling needle guiding tip (3) comprises at least one centering element (33, 34).

6. The drilling apparatus (10) according to claim 1, wherein the deflector attachment (1) comprises a curved guide (5) extending from the holder (7) to an exit opening of the deflector housing (2) at a second end of the deflector attachment (1), wherein a drilling needle guiding tip (3) is arranged at the exit opening, wherein the opposed ends of the curved guide (5) are held by holder rings.

7. The drilling apparatus (10) according to claim 1, wherein the deflector attachment (1) comprises a plurality of individual guides (5') arranged along a curvature course provided for the drilling needle (19) in the deflector housing (2) between the holder (7) and an exit opening of the deflector housing (2) at a second end of the deflector attachment (1).

8. The drilling apparatus (10) according to claim 1, wherein the deflector attachment (1) comprises a curved guide (5) extending from the holder (7) to an exit opening of the deflector housing (2) at a second end of the deflector attachment (1), wherein a drilling needle guiding tip (3) is arranged at the exit opening, wherein the opposed ends of the curved guide (5) are held by holder rings, wherein the deflector attachment (1) further comprises a plurality of individual guides (5') arranged along a curvature course provided for the drilling needle (19) in the deflector housing (2) between the holder (7) and the exit opening of the deflector housing (2) at the second end of the deflector attachment (1).

9. A method for carrying out drilling or drilling resistance measurements at a predetermined location of an object (100) by using a drilling apparatus (10) according to claim 1, the method comprising:

arranging and fastening the deflector attachment (1) at a front side of the device housing (12) by engaging first fastening means provided at the deflector attachment (1) and second fastening means provided at the device housing (12);

exchanging a drilling needle of the drilling device (111) or of the drilling resistance measuring device (11) for an elongated drilling needle (19) that is extended by a length of the deflector attachment (1);

placing the drilling apparatus (10) with the deflector attachment (1) against a predetermined location of the object (100) so that the drilling needle exit axis (a) of the deflector attachment (1) is arranged at a predetermined angular position in relation to a longitudinal axis (s) or a surface plane at the predetermined location of the object (100); and carrying out drilling or drilling resistance measurement by allowing a section of the elongated drilling needle (19) exiting from the deflector attachment (1) along the drilling needle exit axis ($\alpha$) to penetrate at the predetermined location of the object (100) into the object (100), wherein the elongated drilling needle (19) is deflected by the deflector attachment (1) about the predetermined angle ($\alpha$) in relation to the drill axis (b).

10. The method according to claim 9, further comprising, prior to arranging and fastening the deflector attachment (1), the steps of:

determining an angle ($\alpha$) and predetermining a length of a suitable deflector attachment based on a position of the location of the object (100) where drilling or a drilling resistance measurement is to be carried out;

selecting a deflector attachment from a set of two or more deflector attachments based on the angle ($\alpha$), the predetermined length, and/or predetermined fastening means (40);

removing a deflector attachment (1) or a front cover currently arranged at the drilling device (111) or the drilling resistance measuring device (11).

* * * * *